United States Patent
Gao et al.

(10) Patent No.: US 10,457,702 B2
(45) Date of Patent: Oct. 29, 2019

(54) DICAFFEOYL SPERMIDINE CYCLIZED DERIVATIVES AND USE THEREOF

(71) Applicant: Jinan University, Guangzhou, Guangdong (CN)

(72) Inventors: Hao Gao, Guangdong (CN); Xinsheng Yao, Guangdong (CN); Rongrong He, Guangdong (CN); Guodong Chen, Guangdong (CN); Zhengqun Zhou, Guangdong (CN); Chuanxi Wang, Guangdong (CN); Dan Hu, Guangdong (CN); Hongxia Fan, Guangdong (CN)

(73) Assignee: Jinan University, Guangzhou, Guangdong (CN)

( * ) Notice: Subject to any disclaimer, the term of this patent is extended or adjusted under 35 U.S.C. 154(b) by 0 days.

(21) Appl. No.: 16/070,667

(22) PCT Filed: Jan. 13, 2017

(86) PCT No.: PCT/CN2017/071116
§ 371 (c)(1),
(2) Date: Jul. 17, 2018

(87) PCT Pub. No.: WO2017/124969
PCT Pub. Date: Jul. 27, 2017

(65) Prior Publication Data
US 2019/0031701 A1    Jan. 31, 2019

(30) Foreign Application Priority Data
Jan. 19, 2016  (CN) .......................... 2016 1 0033609

(51) Int. Cl.
| | | |
|---|---|---|
| *A61K 31/7016* | (2006.01) | |
| *A61K 31/7034* | (2006.01) | |
| *A61K 31/7052* | (2006.01) | |
| *A61P 25/28* | (2006.01) | |
| *A61P 25/16* | (2006.01) | |
| *C07H 15/24* | (2006.01) | |
| *C07H 1/08* | (2006.01) | |
| *C07H 17/02* | (2006.01) | |

(52) U.S. Cl.
CPC ......... *C07H 15/24* (2013.01); *A61K 31/7016* (2013.01); *A61K 31/7034* (2013.01); *A61K 31/7052* (2013.01); *A61P 25/16* (2018.01); *A61P 25/28* (2018.01); *C07H 1/08* (2013.01); *C07H 17/02* (2013.01)

(58) Field of Classification Search
None
See application file for complete search history.

(56) References Cited

U.S. PATENT DOCUMENTS

2003/0162789 A1    8/2003  Park et al.

FOREIGN PATENT DOCUMENTS

| CN | 103735728 A | 4/2014 | |
|---|---|---|---|
| CN | 104276973 A | 1/2015 | |
| CN | 105646619 A | 6/2016 | |
| WO | WO-2010014245 A1 * | 2/2010 | ........... A61K 36/815 |

OTHER PUBLICATIONS

Patent Cooperation Treaty, International Search Report and Written Opinion for International Application No. PCT/CN2017/071116 dated Apr. 17, 2017, 14 pages.
Jin, Hongli, et al., "Preparative separation of a challenging anthocyanin from Lycium ruthenicum Murr. by two-dimensional reversed-phase liquid chromatography/hydrophilic interaction chromatography," The Royal Society of Chemistry, 2015, vol. 5, pp. 62134-62141.
Tully, Tim, and Quinn, William G., "Classical conditioning and retention in normal and mutant Drosophila melanogaster," Journal of Comparative Physiology A, 1985, vol. 157, pp. 263-277.
Tully, T., et al., "Genetic Dissection of Consolidated Memory in Drosophila," Cell, 1994, vol. 79, pp. 35-47.
Yin, J. C. P., et al., "Induction of a Dominant Negative CREB Transgene Specifically Blocks Long-Term Memory in Drosophila," Cell, 1994, vol. 79, pp. 49-58.
Parr, Adrian J., et al., "Dihydrocaffeoyl Polyamines (Kukoamine and Allies) in Potato (Solanum tuberosum) Tubers Detected during Metabolite Profiling," Journal of Agricultural and Food Chemistry, 2005, vol. 53, pp. 5461-5466.
Zhou, Zheng-Qun, et al., "Lycibarbarspermidines A-O, New Dicaffeoylspermidine Derivatives from Wolfberry, with Activities against Alzheimer's Disease and Oxidation," Journal of Agricultural and Food Chemistry, 2016, vol. 64., pp. 2223-2237.

* cited by examiner

*Primary Examiner* — Traviss C McIntosh, III
(74) *Attorney, Agent, or Firm* — Fitch, Even, Tabin & Flannery, LLP

(57) ABSTRACT

The present invention relates to dicaffeoyl spermidine cyclized derivatives and a preparation method and use thereof. Biological activity experiments show that the dicaffeoyl spermidine cyclized derivatives of the present invention have anti-Senile dementia activity and antioxidant activity, and their activity are even better than that of a positive control drug, thus suitable for the prevention and treatment of neurodegenerative diseases such as Senile dementia.

9 Claims, No Drawings

DICAFFEOYL SPERMIDINE CYCLIZED DERIVATIVES AND USE THEREOF

CROSS-REFERENCE TO RELEATED APPLICATIONS

This application is a U.S. national phase application filed under 35 U.S.C. § 371 of International Application Number PCT/CN2017/071116, filed Jan. 13, 2017, designating the United States, which claims priority from Japanese Patent Application Number 201610033609.8, filed Jan. 19, 2016.

TECHNICAL FIELD

The present invention belongs to the field of natural medicines, and more specifically relates to dicaffeoyl spermidine cyclized derivatives and use thereof for preventing and treating neurodegenerative diseases.

BACKGROUND OF THE INVENTION

Neurodegenerative diseases are one kind of chronic, progressive neurological diseases, generally characterized by delayed neuronal degenerative lesion and cell loss in specific regions. It is caused by the loss of neurons or their myelin sheath, and will worsen over time, resulting in dysfunction. The neurodegenerative diseases are generally divided into two categories according to their phenotype, one is affecting movement, such as cerebellar ataxia, Parkinson's disease, and the other is Dementia that affects memory and its related function. At present, the therapeutic drug for neurodegenerative diseases is still fewer.

Senile dementia is one of the neurodegenerative diseases, and is heterogeneous disease with multiple etiologies. It is a central nervous system degenerative disease syndrome characterized by progressive cognitive dysfunction and memory impairment, behaving as a decrease in intelligence (including memory, learning ability, direction recognition ability, language ability, comprehension and judgment ability). This disease is affected by many factors (including biological and psychosocial factors). There are as many as 30 possible pathogenetic factors and hypotheses, such as family history, head trauma, thyroid disease, and viral infection. Senile dementia is commonly seen as Alzheimer's disease (AD), Vascular dementia (VA), Dementia with Lewy bodies (DLB), and Frontotemporal dementia (FTD). In all patients with dementia, Alzheimer's disease accounted for 50 to 70%, which is the most common type of Senile dementia.

The treatment of Senile dementia is mainly divided into: (1) the symptomatic treatment by controlling the concomitant psychopathological states with the medication mainly including anxiolytic drugs such as alprazolam, oxazepam, triazolam; antidepressants, such as Prozac, paroxetine, sertraline; antipsychotics such as risperidone, olanzapine, (2) the improvement of intelligence or cognitive function with the medication mainly including acetylcholinesterase inhibitors, N-methyl-D-aspartate receptor antagonists (NMDA), estrogens, and drugs for promoting brain metabolism. These drugs can improve the patient's dementia symptoms to a certain extent, but they cannot fundamentally prevent the deterioration of the disease and reverse the disease. Therefore, the search for anti-Senile dementia drugs has attracted worldwide attention, and many related biological activity screening and evaluation systems have been established. Among numerous existing whole animal models, fruit fly is one of the most well-known model organisms. The fruit fly has advantages that cannot be matched by other animal models, for example, extremely small individual space occupancy (in general, thousands fruit flies can be cultured in a single reagent bottle), low feeding costs, easy culture, rapid reproduction and strong reproductive capacity (high screening throughput), low sample consumption (5-50 mg), short life cycle (about 50 days, short activity test cycle), evident age-related neuronal deterioration. Thus it is desired model for the study and drug screening for neurodegenerative diseases such as Senile dementia.

Dicaffeoyl spermidine derivatives are a rare class of plant components that are currently under-researched. There have been no previous reports on dicaffeoyl spermidine cyclized derivatives. The present invention is the discovery and isolation of a class of dicaffeoyl spermidine cyclized derivatives from fructus lycii, and has been demonstrated by the fruit fly model that it has the activity of preventing and treating neurodegenerative diseases, especially senile dementia.

SUMMARY OF THE INVENTION

An object of the present invention is to provide a class of dicaffeoyl spermidine cyclized derivatives having the following structure formula, or pharmaceutically acceptable salts thereof,

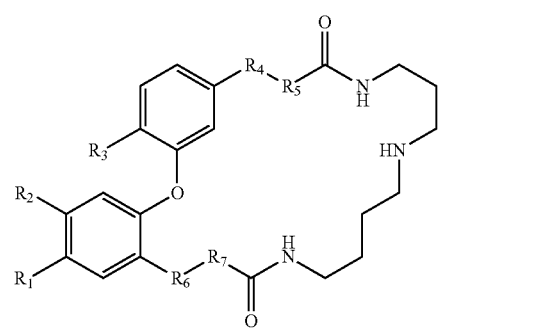

Formula (I)

wherein, $R_1$, $R_2$, and $R_3$ are hydroxy, methoxy, or optionally substituted glycosyl, $R_4$ and $R_5$ are both —CH= or —CH$_2$—, $R_6$ and $R_7$ are both —CH= or —CH$_2$—. The optionally substituted is optionally substituted with one or more of the following glycosyl groups: various monosaccharide groups such as glucosyl, glucuronyl, mannosyl, galactosyl, allosyl, fmctosyl, sorbosyl, furanosyl, rhamnosyl, quinovosyl, arabinosyl, lyxosyl, xylosyl, ribosyl, and various disaccharide groups and polysaccharide groups formed by the above monosaccharides.

In a further embodiment of the present invention, the compound of formula (I) is preferably a compound having the following structural formula:

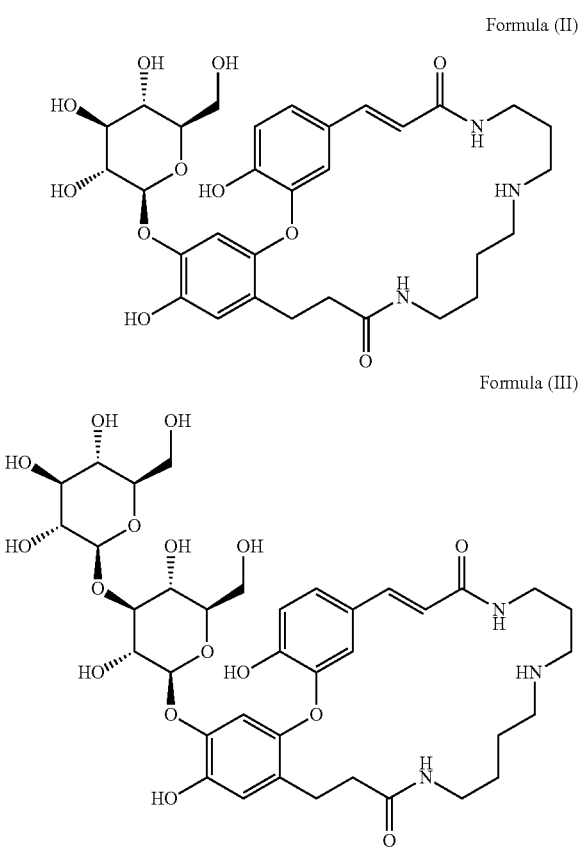

Formula (II)

Formula (III)

In the present invention, the pharmaceutically acceptable salts of the dicaffeoyl spermidine cyclized derivatives of the formula (I) are salts formed by the dicaffeoyl spermidine cyclized derivatives of the formula (I) with inorganic acids such as hydrochloric acid, hydrobromic acid, sulfuric acid, nitric acid, or organic acids such as trifluoroacetic acid, acetic acid, propionic acid, malonic acid, butyric acid, lactic acid, methanesulfonic acid, ethanesulfonic acid, benzenesulfonic acid, p-toluenesulfonic acid, maleic acid, benzoic acid, succinic acid, picric acid, tartaric acid, citric acid, fumaric acid.

Another object of the present invention is to provide a use of dicaffeoyl spermidine cyclized derivatives and the pharmaceutically acceptable salts thereof in a medicament for preventing or treating neurodegenerative diseases, including but not limited to one or more of senile dementia, Parkinson's disease, multiple sclerosis and Huntington's disease, preferably senile dementia, more preferably, the senile dementia is Alzheimer's disease, vascular dementia, dementia with Lewy body or frontotemporal dementia.

The dicaffeoyl spermidine cyclized derivatives were isolated from the fructus lycii which is a fruit of Lycium barbarum. The fructus lycii was collected from Zhongning County, Ningxia Hui Autonomous Region, China The samples were kept at the Institute of Traditional Chinese Medicine and Natural Medicines, College of Pharmacy, Jinan University (No. LYBA-2013-NX-ZN, Location: College of Pharmacy, Jinan University, 601 Huangpu Road West, Guangzhou 510632, China).

The method for preparing the dicaffeoyl spermidine cyclized derivatives and the pharmaceutically acceptable salts thereof specifically includes the following steps:

(1) The fructus lycii was extracted 3 times for 2 hours each time by heating under reflux with ethanol-water having the volume ratio of 60:40. After filtration, the filtrate was concentrated under reduced pressure to obtain a concentrated solution.

(2) The concentrated solution was chromatographed through a macroporous resin column and eluted successively with ethanol-water having the volume ratios of 0:100, 30:70, 50:50, 70:30, and 95:5 to obtain 5 fractions of F1, F2, F3, F4, and F5.

(3) The fraction F2, obtained by the elution with ethanol-water having the volume ratio of 30:70, was subjected to a silica gel column chromatography under normal pressure, and eluted successively with chloroform-methanol-water having the volume ratios of 95:5:0, 90:10:1, 85:15:1.5, 80:20:2, 70:30:3, 60:40:4, 50:50:5, 40:60:6 and 0:100:0 to obtain a total of 10 sub-fractions of F2.1, F2.2, F2.3, F2.4, F2.5, F2.6, F2.7, F2.8, F2.9 and F2.10.

(4) The sub-fraction F2.9, obtained by the elution with chloroform-methanol-water having the volume ratio of 40:60:6, was subjected to a low-medium pressure liquid phase ODS column chromatography, and eluted successively with methanol-water-trifluoroacetic acid having the volume ratios of 5:95:0.1, 10:90:0.1, 15:85:0.1, 20:80:0.1, 25:75:0.1, 30:70:0.1, 40:60:0.1 and 100:0:0 to obtain a total of 9 sub-fractions of F2.9.1, F2.9.2, F2.9.3, F2.9.4, F2.9.5, F2.9.6, F2.9.7, F2.9.8 and F2.9.9.

(5) The sub-fraction F2.9.6, obtained by the elution with methanol-water-trifluoroacetic acid having the volume ratio of 15:85:0.1, was subjected to a reversed phase preparative HPLC, and eluted with methanol-water-trifluoroacetic acid having the volume ratio of 20:80:0.1 at a flow rate of 8 mL/min, to obtain the dicaffeoyl spermidine cyclized derivatives of the present invention.

Still another object of the present invention is to provide a pharmaceutical composition for preventing or treating neurodegenerative diseases, which comprises compounds of formula (I) or pharmaceutically acceptable salts thereof as active ingredients and pharmaceutically acceptable excipients.

Preferred compounds of formula (I) are compounds of formula (II) or formula (III), or pharmaceutically acceptable salts thereof, the pharmaceutically acceptable excipients include, but are not limited to, diluents, lubricants, binders, disintegrants, stabilizers, solvents, and the like.

The diluents of the present invention include but are not limited to starch, microcrystalline cellulose, sucrose, dextrin, lactose, powdered sugar, glucose, and the like.

The lubricants include but are not limited to magnesium stearate, stearic acid, sodium chloride, sodium oleate, sodium lauryl sulfate, poloxamer, and the like.

The binders include but are not limited to water, ethanol, starch slurry, syrup, hydroxypropyl methylcellulose, sodium carboxymethylcellulose, sodium alginate, polyvinylpyrrolidone, and the like.

The disintegrants include but are not limited to starch effervescent mixtures, i.e., sodium bicarbonate and citric acid, tartaric acid, low substituted hydroxypropyl cellulose, and the like.

The stabilizers include but are not limited to polysaccharides such as acacia, agar, alginic acid, cellulose ether, and carboxymethyl chitin, and the like.

The solvents include but are not limited to water, balanced salt solution, and the like.

The pharmaceutical composition of the present invention may be administered orally or by injection. The corresponding dosage form of the pharmaceutical composition includes, but is not limited to, solid oral formulations, liquid oral formulations, injections and the like.

The preferred solid oral formulations include tablets, granules, capsules, dripping pills, powders, and the like. The liquid oral formulations include oral liquids, emulsions, and the like. The injections include small water injections, large infusions, lyophilized powders for injection, and the like.

More preferred tablets include dispersible tablets, enteric tablets and the like.

The formulations of the present invention can be prepared according to conventional techniques in the pharmaceutical arts.

The amount of the active ingredient (i.e., the compound of the present invention) contained in the pharmaceutical formulation of the present invention can be used specifically according to the condition of the patient and the doctor's diagnosis. The dose or concentration of the active compound is adjusted within a relatively wide range. The content of the active compound ranges from 1% to 90% by weight of the pharmaceutical composition.

Beneficial Effects:

Compared with the prior art, the present invention has the following advantages and beneficial effects: the dicaffeoyl spermidine cyclized derivatives shown in the present invention are novel dicaffeoyl spermidine cyclized derivatives. The present invention demonstrated by the biological activity test experiment that the dicaffeoyl spermidine cyclized derivatives of the present invention have anti-Senile dementia activity and anti-oxidant activity, and their activity is even better than that of a positive control drug or equivalent to the positive control drug. They can significantly improve the cognitive function of patients with Senile dementia, thus are suitable for the prevention and treatment of Senile dementia and neurodegenerative diseases.

DETAILED DESCRIPTION OF THE INVENTION

The following examples are intended to illustrate the invention without limiting it further. The present invention can be implemented in any of the ways described in the Summary of the Invention.

In the following examples, the mass spectrometer was a LCQ Advantage MAX mass spectrometer manufactured by Finnigan, Germany. The superconducting NMR spectrometer was a Bruker AV-600. Column chromatography HP-20 macroporous resin is a product of Japan's Mitsubishi Corporation. Thin-layer chromatography silica gel GF254 and column chromatography silica gel (200-300 mesh) are products of Qingdao Ocean Chemical Factory. The reversed phase ODS filler (50 µm) is a product of YMC Japan. The low-medium pressure liquid chromatography is a product of Shanghai Lisui Electronic Technology Co., Ltd. The preparative column used for the liquid phase separation was a Cosmosil Packed $C_{18}$ column (20.0×250 mm, 5 µm). The methanol for liquid chromatography is chromatographic grade, the water is double distilled water, and the other reagents are analytical grade.

EXAMPLE 1

Preparation of Compounds of Formula (II) and Formula (III)

The 19.5 kg fmctus lycii was extracted 3 times for 2 hours each time by heating under reflux with 100L ethanol-water (60:40, v/v). After filtration, the filtrate was concentrated under reduced pressure to obtain a concentrated solution. The concentrated solution was chromatographed through a macroporous resin column, and eluted successively with ethanol-water having the volume ratios of 0:100, 30:70, 50:50, 70:30, and 95:5, and 5 fractions of F1, F2, F3, F4, F5 were obtained. Then the fraction F2, obtained by the elution with ethanol-water having the volume ratio of 30:70, was subjected to a silica gel column chromatography under normal pressure by using 70.0 g of F2, and eluted successively with chloroform-methanol-water having the volume ratios of 95:5:0, 90:10:1, 85:15:1.5, 80:20:2, 70:30:3, 60:40:4, 50:50:5, 40:60:6 and 0:100:0, a total of 10 sub-fractions of F2.1, F2.2, F2.3, F2.4, F2.5, F2.6, F2.7, F2.8, F2.9 and F2.10 were obtained. Subsequently, the sub-fraction F2.9 (3.8g), obtained by the elution with chloroform-methanol-water having the volume ratio of 40:60:6, was subjected to a low-medium pressure liquid phase ODS column chromatography, and eluted successively with methanol-water-trifluoroacetic acid having the volume ratio of 5:95:0.1, 10:90:0.1, 15:85:0.1, 20:80:0.1, 25:75:0.1, 30:70:0.1, 40:60:0.1 and 100:0:0, a total of 9 sub-fractions of F2.9.1, F2.9.2, F2.9.3, F2.9.4, F2.9.5, F2.9.6, F2.9.7, F2.9.8 and F2.9.9 were obtained. The sub-fraction F2.9.6 (105.5 mg), obtained by the elution with methanol-water-trifluoroacetic acid having the volume ratio of 15:85:0.1, was subjected to a reversed phase preparative HPLC, and eluted with methanol-water-trifluoroacetic acid (20:80:0.1, v/v/v) at a flow rate of 8 mL/min, the trifluoroacetate salts of the compound of formula (II) ($t_R$: 24.5 min, 12.3 mg, purity 95%) and compound of formula (III) ($t_R$: 29.2 min, 5.1 mg, purity 95%) were obtained.

The physicochemical constants are as follows:

The trifluoroacetate salt of the compound of formula (II): green oily liquid; $[\alpha]_D^{27}$ −23.8 (c 0.50, MeOH); UV (MeOH) $\lambda_{max}$ (log ε) 204 (4.33), 294 (3.95), 320 (3.92) nm; IR (KBr) $\nu_{max}$ 3375, 2933, 2873, 1679, 1508, 1432, 1287, 1200, 1132, 1077, 801, 722 cm$^{-1}$; ESIMS (positive) m/z 632.6; ESIMS (negative) m/z 630.4; HRESIMS (positive) m/z 632.2820 (calcd. for $C_{31}H_{42}N_3O_{11}$, 632.2819), and the molecular formula of the compound (II) was identified as $C_{31}H_{41}N_3O_{11}$; $^{13}C$ and $^{1}H$ NMR are shown in Table 1.

The trifluoroacetate salt of the compound of formula (III): green oily liquid; $[\alpha]_D^{27}$ −25.0 (c 0.50, MeOH); UV (MeOH) $\lambda_{max}$ (log ε) 204 (4.29), 293 (3.85), 319 (3.82) nm; IR (KBr) $\nu_{max}$ 3347, 2935, 2874, 1678, 1508, 1432, 1282, 1199, 1132, 1073, 801, 722 cm$^{-1}$; ESIMS (positive) m/z 794.7; ESIMS (negative) m/z 792.6; HRESIMS (positive) m/z 794.3362 (calcd. for $C_{37}H_{52}N_3O_{16}$, 794.3348), and the molecular formula of the compound (III) was identified as $C_{37}H_{51}N_3O_{16}$; $^{13}C$ and $^{1}H$ NMR are shown in Table 1.

TABLE 1

$^{13}C$ NMR and $^{1}H$ NMR data and attributions of compounds of formula (II) and (III).

| No. | Formula II | | Formula III | |
| --- | --- | --- | --- | --- |
| | $\delta_C^a$ | $\delta_H^a$ | $\delta_C^a$ | $\delta_H^a$ |
| 1 | | 8.17, t (5.6) | | 8.16, t (5.8) |
| 2 | 35.3 | 3.25, m | 35.2 | 3.24, m |
| 3 | 25.4 | 1.73, quint (6.0) | 25.4 | 1.73, quint (6.4) |
| 4 | 42.9 | 2.84, m | 42.9 | 2.83, m |
| 5 | | 8.44, br s | | 8.37, br s |
| 6 | 45.4 | 2.86, m | 45.4 | 2.86, m |
| 7 | 22.2 | 1.51, quint (6.8) | 22.2 | 1.51, quint (6.8) |
| 8 | 25.8 | 1.38, quint (7.4) | 25.8 | 1.38, quint (6.5) |
| 9 | 38.1 | 3.03, q (5.9) | 38.1 | 3.03, m |

TABLE 1-continued $^{13}$C NMR and $^1$H NMR data and attributions of compounds of formula (II) and (III).

| | Formula II | | Formula III | |
|---|---|---|---|---|
| No. | $\delta_C{}^a$ | $\delta_H{}^a$ | $\delta_C{}^a$ | $\delta_H{}^a$ |
| 10 | | 7.68, t (5.2) | | 7.67, t (5.3) |
| 1' | 126.3 | | 126.2 | |
| 2' | 115.2 | 6.84, d (1.8) | 115 | 6.83, d (2.0) |
| 3' | 147.1 | | 147.2 | |
| 4' | 149 | | 149 | |
| 5' | 116.7 | 6.90, d (8.2) | 116.6 | 6.90, d (8.2) |
| 6' | 123.7 | 7.08, dd (8.3, 1.7) | 123.6 | 7.08, dd (8.3, 1.9) |
| 7' | 139.1 | 7.26, d (15.7) | 139.2 | 7.26, d (15.7) |
| 8' | 118.7 | 6.21, d (15.8) | 118.6 | 6.21, d (15.7) |
| 9' | 166.2 | | 166.2 | |
| 1'' | 127.6 | | 127.8 | |
| 2'' | 116.8 | 6.82, br s | 116.9 | 6.83, s |
| 3'' | 143.6 | | 143.7 | |
| 4'' | 144 | | 143.8 | |
| 5'' | 109.8 | 6.68, s | 109.9 | 6.68, s |
| 6'' | 145.3 | | 145.1 | |
| 7'' | 23.3 | 2.70, m | 23.3 | 2.70, t (7.2) |
| 8'' | 35.2 | 2.33, t (7.0) | 35.1 | 2.33, t (7.3) |
| 9'' | 171.2 | | 171.1 | |
| 1''' | 102.3 | 4.59, d (7.5) | 101.3 | 4.77, d (7.3) |
| 2''' | 73.2 | 3.23, m | 72.1 | 3.46, m |
| 3''' | 75.8 | 3.23, m | 86.3 | 3.46, m |
| 4''' | 69.4 | 3.17, m | 67.7 | 3.31, m |
| 5''' | 76.9 | 3.17, m | 76.3 | 3.27, m |
| 6''' | 60.3 | 3.53, m, Ha<br>3.44, m, Hb | 60.1 | 3.54, br d (11.0), Ha<br>3.46, m, Hb |
| 1'''' | | | 103.8 | 4.36, d (7.8) |
| 2'''' | | | 73.8 | 3.06, m |
| 3'''' | | | 76.1 | 3.16, m |
| 4'''' | | | 70.1 | 3.04, m |
| 5'''' | | | 76.9 | 3.16, m |
| 6'''' | | | 61.1 | 3.68, br d (10.9), Ha<br>3.39, m, Hb |
| 4'-OH | | 9.88, s | | 9.88, s |
| 3''-OH | | 8.52, s | | 8.55, s |
| 2'''-OH | | 5.46, br s* | | 5.61, d (3.4) |
| 3'''-OH | | 5.06, br s* | | |
| 4'''-OH | | 4.98, br s | | 4.67, d (2.5) |
| 6'''-OH | | 4.44, t (5.2) | | |

$^a\delta$ in ppm, J in Hz, $^1$H NMR (600 MHz), $^{13}$C NMR (150 MHz), in DMSO-d$_6$.
*Assignment may be interchanged.

EXAMPLE 2

Test Method for the Dicaffeoyl Spermidine Cyclized Derivatives in Improving the Activity of Learning and Memory of Senile Dementia Fruit Fly (1) Cultivation of Senile Dementia Fruit Fly W$^{1118}$ (isoCJI), as a background fruit fly of control group in the experiment, was abbreviated as "2U". The fruit flies that successfully introduced with the pathogenic Aβ$_{42}$ protein were (UAS-Aβ$_{42}$; abbreviated as "H29.3"). This strain of fruit flies was hybridized with the fruit fly expressing the Gal4 promoter in whole brain, and the fruit fly strain carrying elav-GAL4$^{c155}$ (P35) and Aβ$_{42}$ was obtained.

(2) Administration of Senile Dementia Fruit Fly

Three groups of drug-free control of healthy fruit fly, drug-free control of disease fruit fly, and dose disease fruit fly were set in the experiment.

All parents of tested fruit flies were housed and propagated at a constant temperature of 24° C. and a humidity of 42% RH (Relative humidity). On the first day after the emergence of the fruit flies, the fruit flies of control group and disease group, as well as the fruit flies to be administered were anesthetized with carbon dioxide, and the fruit flies of the correct characters were selected into the glass tube containing food. During the dosing period, all test fruit flies were kept in an incubator with a constant temperature of 28° C. and a constant humidity of 42% to ensure the drug taking efficiency of the fruit flies. Each day the fruit flies were administered for 4 hours, and the drug was administered from the second day after the fruit flies were selected until the 8th day.

The drugs administered were prepared on the second day after the fruit fly selection, and were administered to the fruit flies on the day of preparation. The drugs were dissolved by 100% DMSO to a concentration of 10 mM. When preparing the working solution, the 10 mM stock solution was diluted to 100 μM with 4% sucrose. In addition, the fruit flies of control group were fed sucrose water containing 1% DMSO. For each Performance Index, two tubes of fruit fly groups are required, each tube containing about 100 fruit flies. Experiments were conducted in a light proof behavior room with constant temperature of 25 ° C., constant humidity of 70%. The method can be found in references [1-3].

1) During the training stage, about 100 flies were loaded into a training tube provided with a copper mesh cross electrode. Two kinds of odors of octanol (OCT) and methylcyclohexanol (MCH) were successively introduced for each 60 s with an intervals for 45 s of fresh air. 60 V pulsed electrical shock stimulation (US, pulse duration 1.5 s, interval 3.5 s) was applied to the fruit flies while introducing the 1$^{st}$ odor. No electrical shock was applied when the second odor (CS−) was introduced. Thereby one training cycle was completed.

2) In the transient memory (learning) ability test, the fruit flies that completed one training cycle were immediately transferred to the selection point of T-Maze, while CS+ and CS− were introduced from the opposite two directions. After two minutes of selection, the fruit flies on both sides were collected separately and counted after anesthesia or sacrifice. The calculation formula for the performance index (PI) is as follows:

PI=[(CS−)−(CS+)]/[(CS−)+(CS+)]×100.

Using OCT and MCH as CS+ for training and testing respectively, the average of the two PIs obtained was used as PI for one experiment. PI=0 indicates that the selection of the fruit flies for the two odors in the test was 50:50, i.e., no memory was formed; PI=100 indicates that the fruit flies in the test all escaped the odor accompanying the electrical shock, i.e., perfect memory. When performing the activity test, the short-term memory deficit tests for the olfactory sensation of the non-administered healthy flies with the same genetic background (2U*H29.3), non-administered Senile dementia disease flies (P35*H29.3), and test drug administered Senile dementia disease flies were also conducted, and their total learning and memory performance indexes (PIs) was calculated respectively. The learning and memory performance index of the test drug administered Senile dementia disease flies was compared with the performance index of the non-administered healthy flies with the same genetic background (2U*H29.3), and the performance index of the non-administered Senile dementia disease flies (P35*H29.3), to evaluate effect of the test drugs against Senile dementia. The relatively higher learning and memory performance index of the test drug administered Senile dementia disease flies indicates stronger effect of the test samples against Senile dementia. One-way analysis of variance (ANOVA) was used for the comparison. As for the learning and memory performance index of the test drug administered Senile dementia disease flies and the learning and memory performance index of the non-administered (only solvent without drug sample was administered) Senile dementia disease flies, P<0.05 means a significant difference, P<0.01 means a very significant difference, P<0.001 means an extremely significant difference.

The data analysis and graphical display were processed by GraphPad Prism 5.01; see Table 2 for detailed results.

TABLE 2

The activity result for the dicaffeoyl spermidine cyclized derivatives in improving the learning and memory of Senile dementia fruit flies

| Genotype/drug | PI (100 μM) |
|---|---|
| 2U*H29.3 | 50.2 ± 1.2 |
| P35*H29.3 | 23.3 ± 3.4# |
| Memantine | 44.2 ± 2.1*** |
| Formula II | 37.1 ± 2.2** |
| Formula III | 45.9 ± 1.9*** |

2U*H29.3 represents a healthy fruit fly; P35*H29.3 represents a disease fruit fly; memantine represents a positive control drug treatment group. The drug treatment group was administered at a concentration of 100 μM. Compared with 2U*H29.3 group, #P < 0.001; compared with P35*H29.3 group, P < 0.01, *P < 0.001; n = 6, One-way analysis of variance (ANOVA).

The experimental results in Table 2 indicate that the compounds of Formula II and Formula III of the present invention can significantly improve the learning and memory function of a Senile dementia fruit fly, wherein the compound of Formula III is superior to the positive control drug in improving the learning and memory function of Senile dementia fruit fly, indicating the dicaffeoyl spermidine cyclized derivatives of the present invention have better effects in preventing and treating Senile dementia.

EXAMPLE 3

Antioxidant Activity Results of Dicaffolyl Spermidine Cyclized Derivatives

The antioxidant activity of the compounds was evaluated by using the oxygen radical absorbance capacity (ORAC) experiment. The detailed experimental procedure is as follows. 0.248 g of AAPH (2,2'-azobisisobutylamidine dihydrochloride) was added to a 50 mL phosphate buffer system to formulate a 18.3 mM AAPH stock solution. 20 μL of phosphate buffer, 20 μL solution of sample to be tested or standard substance Trolox (concentration of 6.25 μM) and 20 μL of fluorescent substance of disodium fluorescein (FL, concentration of 630 nM) were added into the wells of a 96-well plate in order. Then, 140 μL of AAPH (concentration of 18.3 mM) was quickly added to the wells of a 96-well plate, which was immediately placed in a GENios Luciferase based microplate reader manufactured by Tecan, Switzerland, the excitation wavelength was set as 485 nm and the emission wavelength was set as 527 nm. The fluorescence intensity was measured every 2 minutes and recorded for a total of 100 min.

The antioxidant capacity of the active substance is calculated as follows: Relative ORAC value=$(AUC_{sample}-AUC_{blank})/(AUC_{trolox}-AUC_{blank})$. Wherein, $AUC_{sample}$ refers to the integral area under the fluorescence decay curve of the test sample, $AUC_{trolox}$ refers to the integral area under the fluorescence decay curve of the standard substance Trolox, and $AUC_{blank}$ refers to the integral area under the fluorescence decay curve when the test sample or the standard substance Trolox is not added. The detailed results are shown in Table 3:

TABLE 3

Antioxidant activity results of dicaffolyl spermidine cyclized derivatives

| compound | ORAC value (μmol TE/μmol) |
|---|---|
| Formula II | 1.48 ± 0.01 |
| Formula III | 0.96 ± 0.03 |
| EGCG | 1.48 ± 0.02 |

EGCG (epigallocatechin gallate) represents a positive control group.

The experimental results in Table 3 show that the dicaffolyl spermidine cyclized derivatives of the present invention have significant antioxidant activity, wherein the antioxidative effect of the compound of Formula II is comparable to that of the positive control drug.

The present disclosure merely illustrates some of the claimed embodiments, wherein the technical features recited in one or more technical solutions may be combined with any one or more technical solutions, and these technical solutions obtained by combination are also within the claimed scope of the present application, it is as same as these technical solutions obtained by combination have been specifically described in the present disclosure.

REFERENCES

[1] Tully T, et al. *J. Comp. Physiol. A* 1985, 157, 263-277.
[2] Tully T, et al. *Cell* 1994, 79, 35-47.
[3] Yin J C, et al. *Cell* 1994, 79, 49-58.

The invention claimed is:

1. A method for treating a neurodegenerative disease, which comprises administering to a subject in need of treatment a therapeutically effective amount of dicaffeoyl spermidine cyclized derivatives with the following structure formula, or pharmaceutically acceptable salts thereof,

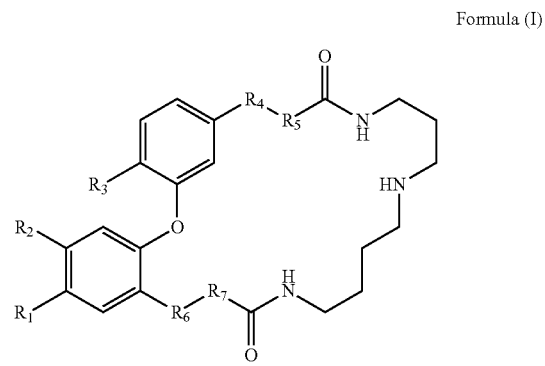

Formula (I)

wherein,
$R_1$, $R_2$, and $R_3$ are hydroxy, methoxy, or optionally substituted glycosyl, $R_4$—$R_5$— is either —CH=CH— or —CH$_2$—CH$_2$—; —$R_6$—$R_7$— is either —CH=CH— or —CH$_2$—CH$_2$—,
wherein the optionally substituted glycosyl is optionally substituted with one or more of monosaccharide groups, disaccharide groups or polysaccharide groups, wherein the monosaccharide groups are selected from the group consisting of:
glucosyl, glucuronyl, mannosyl, galactosyl, allosyl, fructosyl, sorbosyl, furanosyl, rhamnosyl, quinovosyl, arabinosyl, lyxosyl, xylosyl, ribosyl;

wherein the disaccharide groups and polysaccharide groups are formed from the monosaccharides.

2. The method according to claim 1, wherein the pharmaceutically acceptable salts are salts formed by the dicaffeoyl spermidine cyclized derivatives of the formula (I) with an inorganic acid or an organic acid.

3. The method according to claim 2, wherein the inorganic acid is hydrochloric acid, hydrobromic acid, sulfuric acid, or nitric acid, and the organic acid is trifluoroacetic acid, acetic acid, propionic acid, malonic acid, butyric acid, lactic acid, methanesulfonic acid, ethanesulfonic acid, benzenesulfonic acid, p-toluenesulfonic acid, maleic acid, benzoic acid, succinic acid, picric acid, tartaric acid, citric acid, or fumaric acid.

4. The method according to claim 1, wherein the compound of formula (I) is

Formula (II)

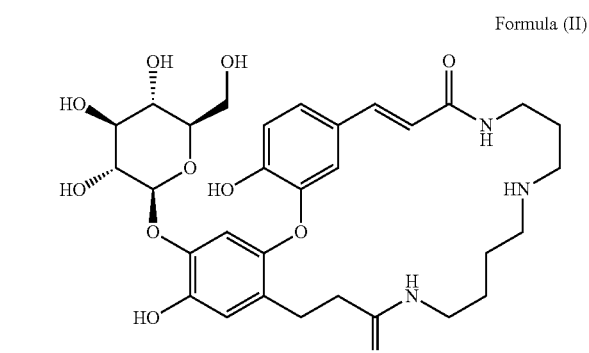

Formula (III)

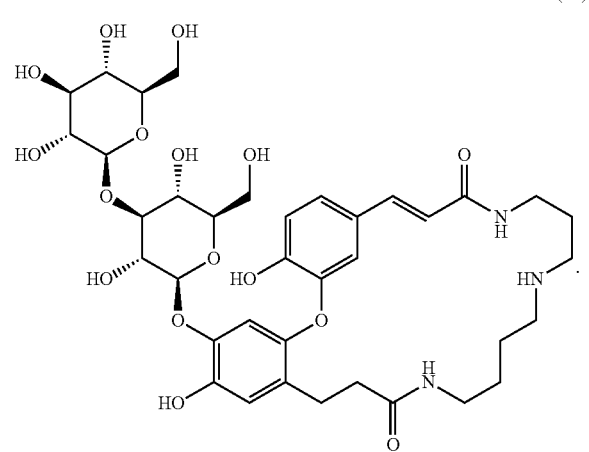

5. The method of claim 1, wherein the dicaffeoyl spermidine cyclized derivatives or the pharmaceutically acceptable salts thereof further comprises pharmaceutically acceptable excipients to provide a pharmaceutical composition.

6. The method according to claim 5, wherein the content of the dicaffeoyl spermidine cyclized derivatives or the pharmaceutically acceptable salts thereof is 1% to 90% by weight of the pharmaceutical composition.

7. The method according to claim 1, wherein the neurodegenerative disease is one or more of senile dementia, Parkinson's disease, multiple sclerosis and Huntington's disease.

8. The method according to claim 7, wherein the neurodegenerative disease is senile dementia, and the senile dementia is Alzheimer's disease, vascular dementia, dementia with Lewy body or frontotemporal dementia.

9. A method for preparing dicaffeoyl spermidine cyclized derivatives or the pharmaceutically acceptable salts thereof comprising the following steps:
(1) The fructus lycii was extracted 3 times for 2 hours each time by heating under reflux with ethanol-water having the volume ratio of 60:40, after filtration, the filtrate was concentrated under reduced pressure to obtain a concentrated solution;
(2) The concentrated solution was chromatographed through a macroporous resin column and eluted successively with ethanol-water having the volume ratios of 0:100, 30:70, 50:50, 70:30, and 95:5 to obtain 5 fractions of F1, F2, F3, F4, F5;
(3) The fraction F2, obtained by the elution with ethanol-water having the volume ratio of 30:70, was subjected to a silica gel column chromatography under normal pressure, and eluted successively with chloroform-methanol-water having the volume ratios of 95:5:0, 90:10:1, 85:15:1.5, 80:20:2, 70:30:3, 60:40:4, 50:50:5, 40:60:6 and 0:100:0 to obtain a total of 10 sub-fractions of F2.1, F2.2, F2.3, F2.4, F2.5, F2.6, F2.7, F2.8, F2.9 and F2.10;
(4) The sub-fraction F2.9, obtained by the elution with chloroform-methanol-water having the volume ratio of 40:60:6, was subjected to a low-medium pressure liquid phase ODS column chromatography, and eluted successively with methanol-water-trifluoroacetic acid having the volume ratios of 5:95:0.1, 10:90:0.1, 15:85:0.1, 20:80:0.1, 25:75:0.1, 30:70:0.1, 40:60:0.1 and 100:0:0 to obtain a total of 9 sub-fractions of F2.9.1, F2.9.2, F2.9.3, F2.9.4, F2.9.5, F2.9.6, F2.9.7, F2.9.8 and F2.9.9;
(5) The sub-fraction F2.9.6, obtained by the elution with methanol-water-trifluoroacetic acid having the volume ratio of 15:85:0.1, was subjected to a reversed phase preparative HPLC, and eluted with methanol-water-trifluoroacetic acid having the volume ratio of 20:80:0.1 at a flow rate of 8 mL/min, to obtain the dicaffeoyl spermidine cyclized derivatives or the pharmaceutically acceptable salts thereof,
wherein the dicaffeoyl spermidine cyclized derivatives have the following formula Formula (I)

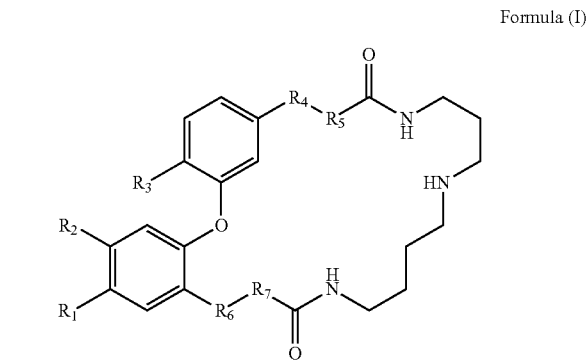

wherein $R_1$, $R_2$, and $R_3$ are hydroxy, methoxy, or optionally substituted glycosyl, —$R_4$—$R_5$— is either —CH=CH or —$CH_2$—$CH_2$—; —$R_6$—$R_7$— is either —CH=CH or —$CH_2$—$CH_2$—,
wherein the optionally substituted glycosyl is optionally substituted with one or more of monosaccharide groups, disaccharide groups or polysaccharide groups, wherein the monosaccharide groups are selected from the group consisting of:

glucosyl, glucuronyl, mannosyl, galactosyl, allosyl, fructosyl, sorbosyl, furanosyl, rhamnosyl, quinovosyl, arabinosyl, lyxosyl, xylosyl, ribosyl;

wherein the disaccharide groups and polysaccharide groups are formed from the monosaccharides.

* * * * *